United States Patent [19]

Goldner et al.

[11] 4,119,712
[45] Oct. 10, 1978

[54] MAKEUP FOUNDATIONS

[75] Inventors: Tibor G. Goldner, Fresh Meadows, N.Y.; Eustace Fotiu, Mahwah, N.J.

[73] Assignee: Revlon, Inc., New York, N.Y.

[21] Appl. No.: 818,432

[22] Filed: Jul. 25, 1977

[51] Int. Cl.$^2$ .................... A61K 7/021; A61K 7/035
[52] U.S. Cl. ........................................ 424/63; 424/69
[58] Field of Search ................ 424/63, 69, 357, 366, 424/358; 260/448.8 AS, 448.8 R

[56] References Cited

U.S. PATENT DOCUMENTS

| 3,250,680 | 5/1966 | Menkart et al. | 424/358 X |
| 3,639,572 | 2/1972 | Heinrich et al. | 424/63 |
| 3,800,034 | 3/1974 | Kircher et al. | 424/63 |
| 3,801,613 | 4/1974 | Swimm | 260/448.8 R X |
| 3,978,205 | 8/1976 | Newman et al. | 424/357 |
| 3,998,973 | 12/1976 | Carlson | 424/357 |
| 4,000,317 | 12/1976 | Menda et al. | 424/69 X |

FOREIGN PATENT DOCUMENTS 45-12,154  2/1970  Japan ...................................... 424/357

*Primary Examiner*—Albert T. Meyers
*Assistant Examiner*—H. Steven Seifert

[57] ABSTRACT

A stable, long-wearing makeup foundation containing hydrophobic and hydrophilic silicas.

3 Claims, No Drawings

MAKEUP FOUNDATIONS

The present invention relates to cosmetic compositions, and particularly relates to makeup foundations.

Makeup foundations are used in cosmetology to provide bases for obtaining proper adhesion of powder and pigments to skin. Such compositions comprise a mixture of oils, fats, waxes and the like in which there have been uniformly dispersed dry powders, such as talc, and pigments.

The makeup foundations now in use have poor wear and color stability so that in a few hours after the application the preparation begins to wear off the skin and to change color ("orange out"). These effects result from the interaction of perspiration, skin oils and surface moisture of the skin with the oils, pigments and powders in the foundation.

It is accordingly an object of the present invention to provide a makeup foundation which has long wear and adhesion.

It is another object of the present invention to provide a makeup foundation containing pigments, which has good color stability for several hours after application.

It is a further object of the present invention to provide a makeup foundation having long wear and adhesion and color stability of the pigments, which can be readily and inexpensively prepared from readily available raw materials.

It is still another object of the present invention to provide foundations which may contain water and still have long wear, adhesion and color stability.

In accordance with the present invention it has been found that the addition to makeup foundations of a mixture of hydrophobic fumed silica and hydrophilic fumed silica impart to these foundations long wear, adhesion and color stability.

Hydrophobic fumed silica is an inorganic powdered silica of low bulk density. It is derived from a 99.8% pure fumed silica in which the hydrophilic hydroxyl groups are replaced by trimethylsiloxyl groups. This replacement imparts a number of unique characteristics to the powder, including dry lubricant capabilities and an extremely high degree of water repellency. The submicron particle size and large organic surface area enable it to impart its own properties to those of other systems even when present in concentrations as low as 0.1% to 2.0% by weight. This product is commercially available under the tradename Tullanox 500 from Tulco, Inc., North Billerica, Massachusetts.

The properties of hydrophobic fumed silica would appear to make it suitable for incorporation into makeup foundations to improve their properties. However, when hydrophobic fumed silica was introduced into the water phase of the foundations, such silica due to its high water repellant character remained separated from and floated on top of the foundation.

I have now found that by introducing a hydrophilic fumed silica along with the hydrophobic fumed silica, it is possible to obtain stable makeup foundations containing water.

As a suitable hydrophilic fumed silica I use Cabosil, available from the Cabot Corporation, Boston, Mass.

In preparing the stable aqueous makeup foundations of the present invention, I use from about 0.03 to 1.0% by weight of hyrophobic fumed silica and from about 0.03 to 0.5% by weight of hydrophilic fumed silica based on the total weight of the makeup foundation. Any aqueous makeup foundation such as those described in Balsam and Sagarin, Cosmetics, Science and Technology, Second Ed., Vol. I, Chapter 9, is suitable for use in the practice of the present invention.

While it is possible to prepare the aqueous makeup foundations of the present invention by weighing out the desired amount of each ingredient, mixing all of them and blending till a uniform composition is obtained, I prefer first to prepare a dry pigment system containing talc, pigments, hydrophobic fumed silica and hydrophilic fumed silica, and then add this free-flowing system to the other ingredients of the foundation. These ingredients include water, oils, surfactants which may be ionic or non-ionic, and, if desired, fragrances and colorants.

The dry pigmemt system contains about 5–49% by weight of pigments, about 50 to 90% of weight of talc, about 0.5 to 3% by weight of hydrophilic fumed silica and about 0.5–5% by weight of hydrophobic fumed silica. Any pigment acceptable for cosmetic use may be used. These include titanium dioxide, zinc oxide, ferric oxide, chromic oxide and the like.

The invention will be more fully understood from the examples which follow. These examples are given only by way of illustration and are not to be considered as limiting.

Examples 1 and 2 illustrate the compositions of dry pigment systems. In these and in other examples all numerical values refer to parts by weight.

EXAMPLE 1

| | |
|---|---|
| Talc | 88 |
| Titanium dioxide | 10 |
| Hydrophobic fumed silica | 1 |
| Hydrophilic fumed silica | 1 |

The talc and titanium dioxide were intimately mixed with the hydrophilic and hydrophobic fumed silicas in a suitable blender until the powder was uniformly blended. The blend was then micropulverized through a fine screen (using a powder micropulverizer) to obtain a uniformly distributed blend. This dry pigment system is free-flowing and readily dispensible in water.

EXAMPLE 2

| | |
|---|---|
| Talc | 52 |
| Ferric oxide | 40 |
| Hydrophobic fumed silica | 5 |
| Hydrophilic fumed silica | 3 |

This mixture was prepared using the procedure of Example 1.

Examples 3 to 5 illustrate makeup foundations of the present invention. These foundations may be either in the form of oil-in-water or water-in-oil emulsions; examples 3 and 4 showing oil-in-water emulsions and example 5 a water-in-oil emulsion. Example 6 illustrates an eyeshadow formulation.

EXAMPLE 3

| | |
|---|---|
| Water | 67.70 |
| Propylene Glycol | 5.00 |
| Carboxymethyl cellulose | 0.10 |
| Magnesium aluminum silicate | 0.50 |
| Triethanolamine | 0.70 |
| Methylparaben | 0.20 |

-continued

| | |
|---|---|
| Treated Lecithin | 0.50 |
| Dry pigment system of Example 1 | 15.00 |
| Mineral oil | 5.00 |
| Stearic acid | 2.00 |
| Lanolin | 2.00 |
| Glycerol monostearate | 1.00 |
| Propyl paraben | 0.10 |
| Fragrance | 0.20 |
| | 100.00 |

EXAMPLE 4

| | |
|---|---|
| Water | 65.0 |
| PPG-10-Lanolin ether | 3.0 |
| Laneth-10-Acetate | 4.0 |
| Isopropyl isostearate | 10.0 |
| Cetyl alcohol | 1.5 |
| Stearyl alcohol | 1.5 |
| Glyceryl stearate and PEG-100 stearate (Arlacel-165) | 3.8 |
| Dry pigmented system of Example 2 | 10.0 |
| Magnesium aluminum silicate | 1.0 |
| Propyl paraben | 0.1 |
| Fragrance | 0.1 |
| | 100.00 |

EXAMPLE 5

| | |
|---|---|
| Water | 67.6 |
| Carboxymethylcellulose | 0.1 |
| Methyl paraben | 0.2 |
| Polyoxyethylene 20 sorbitan monooleate | 0.5 |
| Dry pigmented system of Example 1 | 12.0 |
| Glyceryl oleate and propylene glycol (Arlacel-186) | 3.0 |
| Beeswax | 0.5 |
| Ozokerite | 0.5 |
| Propyl paraben | 0.1 |
| Cyclomethicone | 5.0 |
| Steareth-10 | 1.5 |
| Isopropyl myristate | 5.0 |
| Mineral oil | 4.0 |
| | 100.00 |

EXAMPLE 6

| | | |
|---|---|---|
| Propylene glycol | | 3.0 |
| Carboxymethyl cellulose | | 0.2 |
| Magnesium aluminum silicate | | 1.0 |
| 5-Ethoxy-lauryl ether | | 0.5 |
| Triethanolamine | | 0.7 |
| Dry pigmented system of Example 1 | | 5.0 |
| Ultramarine blue | | 3.0 |
| Stearic acid | | 1.5 |
| Sorbitan monostearate | | 0.5 |
| Ethylhexyl palmitate | | 3.0 |
| Beeswax | | 1.0 |
| Water | q.s. | 100.0 |

The aqueous makeup foundations of the above examples have good skin adhesion, color stability, long wear and free skin transpiration. Six hours after application there was no change in color or appearance of the foundation and it remained on the skin.

We claim:

1. A dry pigment composition for incorporation into aqueous makeup foundations consisting essentially of

| | |
|---|---|
| talc | 50–90%, |
| cosmetically acceptable pigment | 5–49%, |
| hydrophilic fumed silica | 0.5–3%, and |
| hydrophobic fumed silica | 0.5–5% |

2. A dry pigment composition according to claim 1 which contains

| | |
|---|---|
| talc | 88%, |
| titanium dioxide | 10%, |
| hydrophilic fumed silica | 1%, and |
| hydrophobic fumed silica | 1%. |

3. A dry pigment composition according to claim 1 which contains

| | |
|---|---|
| talc | 52%, |
| ferric oxide | 40%, |
| hydrophilic fumed silica | 3%, and |
| hydrophobic fumed silica | 5% |

* * * * *

UNITED STATES PATENT OFFICE
CERTIFICATE OF CORRECTION

Patent No. 4,119,712        Dated October 10, 1978

Inventor(s) Tibor G. Goldner and Eustace Fotiu

It is certified that error appears in the above-identified patent and that said Letters Patent are hereby corrected as shown below:

Column 1, line 59, Change "I" to --- We ---

Column 1, line 63, Change "I" to --- we ---

Column 1, line 66, Change "I" to --- we ---

Column 2, line 10, Change "I" to --- we ---.

Signed and Sealed this

Twenty-fourth Day of April 1979

[SEAL]

Attest:

RUTH C. MASON
Attesting Officer

DONALD W. BANNER
Commissioner of Patents and Trademarks